US008858988B2

(12) United States Patent
Chamberland et al.

(10) Patent No.: US 8,858,988 B2
(45) Date of Patent: Oct. 14, 2014

(54) COMPOSITIONS COMPRISING EXTRACTS OF *BOSWELLIA*, TEA TREE, ALOE AND LAVENDER OIL AND METHODS OF TREATING WOUNDS, BURNS AND SKIN INJURIES THEREWITH

(75) Inventors: Guy Chamberland, Boucherville (CA); Peter Bollen, B-Drongen (BE)

(73) Assignees: CuraPhyte Technologies Inc., Boucherville (CA); Nutriquine N.V., Drongen (BE)

( * ) Notice: Subject to any disclaimer, the term of this patent is extended or adjusted under 35 U.S.C. 154(b) by 0 days.

(21) Appl. No.: 13/505,978

(22) PCT Filed: Nov. 2, 2010

(86) PCT No.: PCT/CA2010/001740
§ 371 (c)(1),
(2), (4) Date: Jul. 26, 2012

(87) PCT Pub. No.: WO2011/054090
PCT Pub. Date: May 12, 2011

(65) Prior Publication Data
US 2012/0308637 A1    Dec. 6, 2012

(30) Foreign Application Priority Data

Nov. 3, 2009   (CA) ..................................... 2684258

(51) Int. Cl.
*A61L 15/00* (2006.01)
*A01N 65/00* (2009.01)
*A61K 9/00* (2006.01)
*A61L 15/16* (2006.01)
*A61K 9/127* (2006.01)
*A61K 9/14* (2006.01)
*A61K 35/14* (2006.01)
*A61K 35/20* (2006.01)
*A61K 35/12* (2006.01)
*A01N 59/16* (2006.01)
*A61L 15/44* (2006.01)
*A61K 36/324* (2006.01)
*A61K 36/886* (2006.01)
*A61K 36/53* (2006.01)
*A61L 15/34* (2006.01)
*A61K 36/61* (2006.01)
*A61L 15/40* (2006.01)

(52) U.S. Cl.
CPC ................. *A61L 15/34* (2013.01); *A61L 15/44* (2013.01); *A61K 36/324* (2013.01); *A61K 36/886* (2013.01); *A61L 2300/62* (2013.01); *A61K 36/53* (2013.01); *A61L 2300/30* (2013.01); *A61K 36/61* (2013.01); *A61L 15/40* (2013.01)
USPC ...... 424/445; 424/195.17; 424/400; 424/447; 424/450; 424/489; 424/529; 424/535; 424/572; 424/642; 424/744

(58) Field of Classification Search
CPC . A61K 2300/00; A61K 45/06; A61K 9/0014; A61K 36/53; A61K 36/61; A61K 36/324; A61K 36/886; A61Q 19/00
See application file for complete search history.

(56) References Cited

U.S. PATENT DOCUMENTS

| 6,579,543 B1 * | 6/2003 | McClung ....................... 424/728 |
| 6,589,516 B1 * | 7/2003 | Eyre et al. ..................... 424/70.1 |
| 2009/0004301 A1 * | 1/2009 | Mazzio et al. ................. 424/730 |

FOREIGN PATENT DOCUMENTS

| CA | 2557968 A1 | 9/2005 | |
| CA | 2583562 A1 | 4/2006 | |
| WO | WO 2006040119 A3 * | 7/2006 | ............. A61K 9/107 |
| WO | WO 2008134712 A2 * | 11/2008 | |

OTHER PUBLICATIONS

Tea tree oil (http://en.wikipedia.org/wiki/Tea_tree_oil (downloaded on Jul. 24, 2013)).*
*Lavandula angustifolia* (http://web.archive.org/web/20090801042327/http://en.wikipedia.org/wiki/Lavandula_angustifolia (archived on Aug. 1, 2009)).*
Gauze (http://web.archive.org/web/20090224214950/http://en.wikipedia.org/wiki/Gauze (archived on Feb. 24, 2009)).*
Abu Bakr Mohammad Bin Zakariyya Al-Razi, Formulation ID: AA12/527, Traditional Knowledge Digital Library Database (TKDL) (1962). *English Translation from Kitaab-al-Haawi-fil-Tibb, vol. XII (9th Century AD), Dayerah-al-Ma'aarif Usmania*, Hyderabad, India, (*First Edition*) p. 236.
Farnsworth et al., "Medicinal Plants in Therapy," *Bulletin of the World Health Organization* 63:965-981 (1985).
Mohammad Akmal Khan, Formulation ID: AH5/253F, Traditional Knowledge Digital Library Database (TKDL) (1909). *English Translation from Qaraabaadeen Azam wa Akmal (20th Century AD), Matba Siddiqi/Matba Mustafai*, Delhi, India, p. 362.
Kerr, "The Use of Essential Oils in Healing Wounds," *International Journal of Aromatherapy* 12:202-206 (2002).
International Search Report and Written Opinion for International Application No. PCT/CA2010/001740, dated Feb. 11, 2011 (12 pages).
International Preliminary Report on Patentability for International Application No. PCT/CA2010/001740 dated May 18, 2012 (8 Pages).

* cited by examiner

*Primary Examiner* — Michael G Hartley
*Assistant Examiner* — Sun Y Kim
(74) *Attorney, Agent, or Firm* — Clark & Elbing LLP

(57) ABSTRACT

Compositions for the treatment of sores, wounds, burns and other traumatized dermal tissues and skin injuries comprising *Boswellia* gum, gel, resin or extract, Tea Tree oil (*Melaleuca* oil), an *Aloe* gel, resin, latex or extract and Lavender oil. The composition may be incorporated into a medical device such as a wound dressing or bandage, or formulated into a topical preparation such as an ointment, lotion or cream.

31 Claims, 1 Drawing Sheet

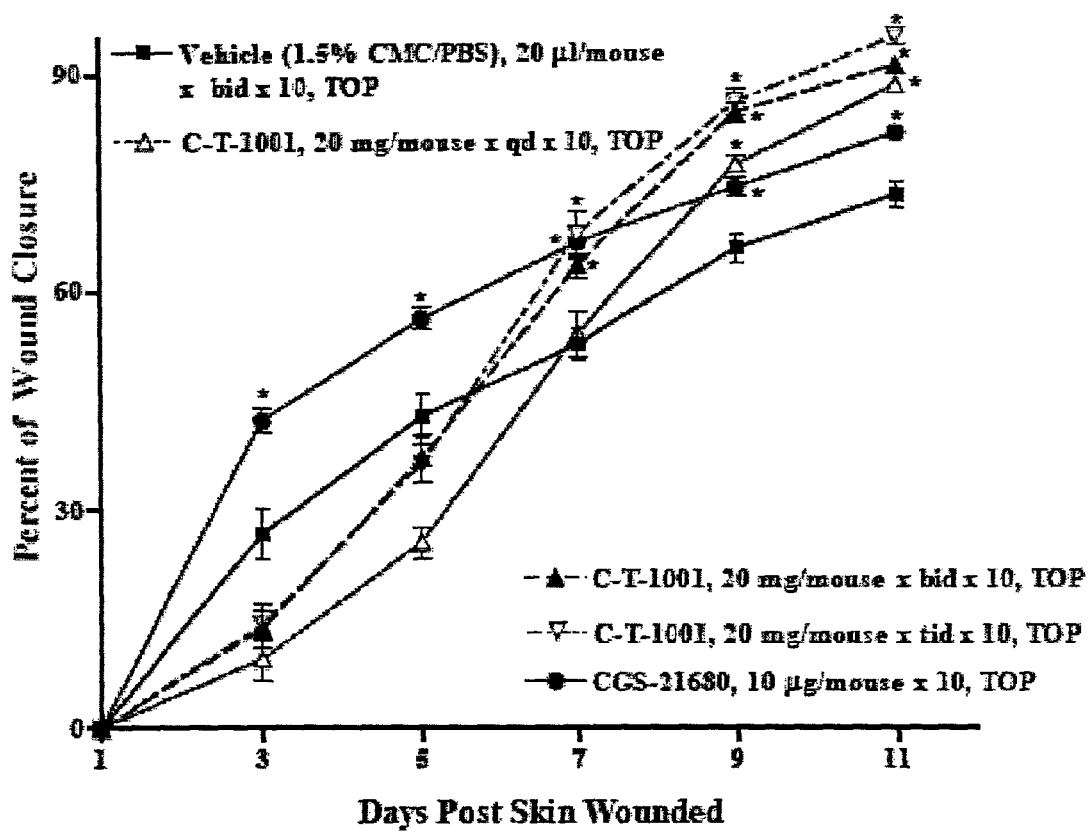

COMPOSITIONS COMPRISING EXTRACTS OF *BOSWELLIA*, TEA TREE, ALOE AND LAVENDER OIL AND METHODS OF TREATING WOUNDS, BURNS AND SKIN INJURIES THEREWITH

FIELD OF INVENTION

The present invention relates to generally to compositions for the treatment of sores, wounds, burns and other traumatized dermal tissues and skin injuries. More specifically, the present invention relates to compositions comprising plant extracts, medical devices incorporating these compositions, and methods of treating sores, wounds, burns and other traumatize dermal tissues and skin injuries therewith.

BACKGROUND OF THE INVENTION

Wound healing is a complex process that some researchers divide into 3 phases of evolution: inflammatory phase, proliferation, and remodeling (1). The inflammatory phase is the first response to an injury and involves multiple responses that include both a cellular and chemokine/cytokine response. The response includes blood coagulation, infiltration of leukocytes, etc. This first phase of response leads to the initiation of the proliferative response for wound healing. In fact, these two first phases overlap and multiple factors influence the phases. An important part of the proliferative phase is the formation of epithelium to cover the wound surface. The epithelialization reaction occurs somewhat in parallel to the growth of granulation tissue that is required to fill the wounds "empty" space. According to Li et al (1), the granulation tissue formation is the result of the proliferation of fibroblasts deposition of collagens and other materials along with an angiogenic process for the formation of new blood vessels. Finally, the third phase is a remodeling phase that involves restoring the structural integrity and functional aspects of the site (1). Every phase of the wound healing process can be influenced by factors such as infection, that will either increase the tissue damage and/or prolong the healing time, as well as dead skin, bleeding, mechanical damage (compression of tissue and friction), dryness, etc.

There are several types of wounds, but they can generally be summarized as either acute or chronic. Acute wounds normally heal without delay and complications, and include burns, traumatic injuries and surgical wounds. Chronic wounds are those that involve a disruption of the wound healing process that results in consequences such as a prolonged time to heal, recurrence or simply non-healing (1). Chronic wounds include venous leg ulcers, pressure sores/ulcers, ischemic ulcers, diabetic ulcers, etc.

Management of Wounds

Each wound is unique and multiple factors influence the methods used to help heal. These factors include the location and size of the injury, the type of injury (e.g. incision, burn), depth of the wound and other tissues involved in injury (i.e., nerves), foreign material in the wound as well as infection, complications during healing that prolong healing time, and genetic or pathophysiological factors influencing the different parameters of healing.

The type of wound closure plays a major role in the healing process. Closure by primary intent is defined as wound closure immediately following the injury and prior to the development of the granulation tissue. Healing by primary intent ultimately leads to the fastest healing and optimal cosmetic result. Closure by secondary intent is defined as the process where wounds heal on their own without surgical closure. Closure by tertiary intent is defined as a first treatment phase where the wound is cleaned and dressings are applied and a second phase several days later for wound closure.

Methods of treating a wound may include one or more steps as necessary to facilitate healing, prevent infection and complications, limit scarring and hyperpigmentation, etc. Treatment may include cleaning the wound to remove foreign material; removing dead skin; closing (in the case of large wounds) with stitching type materials (e.g., sutures); dressing the wound; relieving pain; and treating signs of infection.

In the case of chronic wounds such as pressure or diabetic ulcers, additional treatments may be required. These are generally aimed at trying to improve blood flow to the site of injury to promote healing of the wound/ulcer. Methods involving the use of absorbent dressings and compression bandages typically help improve blood flow.

In addition to the above treatment methods, various substances, both naturally occurring and synthetic, may be employed to promote healing of skin tissues. These are often applied directly to the area of the wound or sore in the form of a lotion or ointment, or incorporated into a bandage, dressing or other device to promote healing while the device is in use.

For example, U.S. Pat. No. 5,266,318 describes a composition for treatment of irradiated skin, open sores, wounds and abrasions. This composition is comprised of an aloe vera gel extract, allantoin and lavender essential oil.

Another composition for the treatment of wounds and related conditions is described in U.S. Pat. No. 5,879,717, which is comprised of a sugar, iodine and a glycol or water vehicle, and is specifically designed for use in veterinary medicine.

A further composition, which is described in U.S. Pat. No. 5,980,875, is prepared by mixing honey with oil, a gelling agent, an emulsifier and other components, and is used for the treatment of Herpes, cold sores, burns, skin allergies and other wounds.

Additionally, U.S. Pat. No. 6,099,866 describes a combination of beeswax with oil and optionally water to produce a composition for treatment of various burns and abrasions.

As can be seen, numerous compositions and combinations are known to assist in the treatment and healing of wounds and skin injury. Nevertheless, research continues in this area in order to develop new compositions with improved effectiveness and/or reduced side-effects.

SUMMARY OF THE INVENTION

An object of the invention is therefore to provide compositions and methods for treating sores, wounds, burns and other traumatized dermal tissues and skin injuries.

The invention accordingly relates to compositions comprising plant extracts useful for treating sores, wounds, burns and other traumatized dermal tissues and skin injuries, as well as medical devices comprising such compositions.

In certain non-limiting embodiments the medical device may be a dressing or a bandage, or may comprise a slow-release polymer, alginate, oligosaccharides (poly-), chitin, or hydrocolloids.

The invention also relates to methods for treating sores, wounds, burns and other traumatized dermal tissues and skin injuries in a subject, comprising administering a composition or medical device as described herein. Preferably, treating a subject with a composition or medical device as defined herein results in at least partial healing or amelioration of the sore, wound, burn or other traumatized dermal tissue or skin injury.

In an embodiment of the invention, the composition comprises *Boswellia* gum, gel, resin or extract, Tea Tree oil (*Melaleuca* oil), *Aloe* gel, resin, latex or extract and Lavender oil.

Without wishing to be limiting, the *Boswellia* gum, gel, resin or extract may be derived from the leaves, plant or roots of *Boswellia serrata* or other species of *Boswellia*, such as *Boswellia sacra* or *Boswellia carterii*. In a preferred embodiment, the composition comprises about 10% to 99% boswellic acids (e.g. as measured by UV-VIS spectrometry analysis, HPLC Diode array or the like).

The Tea Tree oil (*Melaleuca* oil), which is also known as Australian tea tree oil (*Melaleuca alternifolia*) may, in a further non-limiting embodiment, be derived from *Melaleuca* leaves, root or plant and may contain more than >10% terpinene-4-ol (e.g. as measured by GC FID or ECD).

The *Aloe* gel, resin, latex or extract (aqueous or alcoholic extract) may, in a further non-limiting embodiment, be derived from the leaves, root or plant of *Aloe* including, but not limited to *Aloe vera, Aloe africana, Aloe arborescens* Miller, *Aloe barbadensis, Aloe barbadesis,* and *Aloe capensis*.

The Lavender oil may, in a further non-limiting embodiment, be derived from the leaves, root, flower or plant of *Lavandula officinalis* or another species of Lavender such as common lavender, English lavender, garden lavender, *Lavandula angustifolia, Lavandula burnamii, Lavandula dentate, Lavandula dhofarensis, Lavandula latifolia, Lavandula officinalis,* or *Lavandula stoechas*.

In further non-limiting embodiments, the compositions described herein may additionally comprise one or more components or extracts containing growth factors (including but not limited to growth factors from colostrum, whey, blood or tissue), antibiotics, analgesics, zinc oxide, vitamin A, vitamin E, extracts of *Harpagophytum procumens* (Devil's claw) root, *Salix Alba* (White Willow) plant and/or bark, *Tanacetum Parthenium* (Feverfew) herb and/or flower, *Equisetum arvense* (Horsetail), *Spireae ulmaria* (Dropwort), *Betula alba* (Birch), *Urtica dioica* (Stinging Nettle), *Curcumin* extract, *longa* (Tumeric), marine algae, or Gotu kola (*Centella asiatica* Linn.), total triterpenic fraction of *Centella asiatica* (TTECA), or combinations thereof.

The present invention also provides a composition as described above, wherein the composition further comprises one or more components to absorb wound exudates and/or slowly release the active herbal ingredients. These components may include, but are not limited to alginate, hydrocolloid, chitin, polyoligosaccharides, liposome, slow-releasing polymers or agent, or combinations thereof.

The composition as described herein may, in further non-limiting embodiments, be formulated within or on the surface of a medical device. The medical device may be, in certain exemplary embodiments which are also considered to be non-limiting, a dressing, bandage, or other semi-occlusive or occlusive material commonly used in wound care. As an example, the composition may be coated onto the medical device, or embedded or contained within particles or microparticles such as liposomes. For instance, the particles or microparticles comprising the composition as described herein may be used to deliver or release the active herbal ingredients to the wound while maintaining semi-occlusion or complete occlusion.

As mentioned above, the present invention also relates to a method of treating sores, wounds, burns and other traumatized dermal tissues and skin injuries. In certain non-limiting embodiments, the method involves treating acute wounds, such as but not limited to heat and sun burns, traumatic injuries, surgical wounds, punctures, cracked heals, bites, insect bites and infected wounds. In other non-limiting embodiments, the method involves treating chronic wounds, such as but not limited to venous leg ulcers, pressure sores or ulcers, ischemic ulcers and diabetic ulcers. When treating a surgical wound, in a non-limiting embodiment of the described method, the a composition or medical device as described herein may be administered to an incision which has been sutured, or to a wound which has been closed with surgical thread or the like, in order to promote healing of the incision or wound.

According to the methods described herein, the subject may be a mammalian subject, and in further non-limiting embodiments the subject may be a human.

This summary of the invention does not necessarily describe all features of the invention. In addition, those skilled in the art will recognize, or be able to ascertain using no more than routine experimentation, numerous equivalents to the specific procedures described herein. Such equivalents are considered to be within the scope of this invention and are covered by the following claims.

BRIEF DESCRIPTION OF THE FIGURES

Further details of the invention will become apparent from the following description, taken in combination with the appended figure wherein:

FIG. 1 illustrates a plot of the time course of wound healing in mouse cutaneous injury model. Test substance was administered topically (TOP) once or twice or three times daily for 10 consecutive days. The wound closure (%) was determined on days 3, 5, 7, 9 and 11, and then the wound half-closure time ($CT_{50}$) was obtained. One-way ANOVA followed by Dunnett's test was applied for comparison between the treated and vehicle groups. *$P<0.05$, vs. vehicle.

DETAILED DESCRIPTION

Described herein are plant extracts which are useful for treating sores, wounds, burns and other traumatized dermal tissues and skin injuries therewith. The described extracts can be provided in compositions together with an acceptable carrier, and/or together with one or more separate active agents. They can also be incorporated into a medical device as described herein, or used in a method of treating sores, wounds, burns and other traumatized dermal tissues and skin injuries.

The following description is of a preferred embodiment.

According to the present invention, there is provided a composition comprising Boswellia gum, gel, resin or extract, Tea Tree oil (*Melaleuca* oil), an *Aloe* gel, resin, latex or extract and Lavender oil. Other components may also be included as described herein and throughout.

In an embodiment, the *Boswellia* gum, gel, resin or extract is derived from the leaves, plant or roots of *Boswellia serrata*, or other species of *Boswellia* such as *Boswellia sacra, Boswellia carterii*, and contains between about 10% and 99% boswellic acids, for example but not limited to about 10%, 20%, 30%, 40%, 50%, 60%, 70%, 80%, 90%, 99% or any value therein between. The amount of boswellic acids may also be defined by a range of any two of the values listed above or any value therein between, and can be measured, for instance, by UV-VIS spectrometry analysis, HPLC Diode array or other non-limiting method. More preferably the *Boswellia* gum, gel, resin or extract contains between about 50% to 79% boswellic acids.

The Tea Tree oil (*Melaleuca* oil), also known as Australian tea tree oil, may be derived from the leaves, root or plant of

*Melaleuca alternifolia* and, in a non-limiting embodiment contains more than 10% terpinene-4-ol as measured by GC FID, ECD or other non-limiting method comparable thereto (GC: gas chromatography; FID: Flame Ionization Detector; ECD: Electron Capture Detector).

The *Aloe* gel, resin, latex or extract (aqueous or alcoholic extract) may be derived from the leaves, root or plant of *Aloe* (including but not limited to *Aloe vera, Aloe africana, Aloe arborescens* Miller, *Aloe barbadensis, Aloe barbadesis,* or *Aloe capensis*).

The Lavender oil may be derived from the leaves, flower, plant or root of *Lavandula officinalis,* or another species of Lavender such as common lavender, English lavender, garden lavender, *Lavandula angustifolia, Lavandula burnamii, Lavandula dentate, Lavandula dhofarensis, Lavandula latifolia, Lavandula officinalis,* or *Lavandula stoechas.*

The present invention also contemplates compositions comprising components in addition to and outside the ranges provided above.

The composition described herein may also comprise additional components or extracts containing growth factors (such as from colostrum, whey, blood or tissue), antibiotics, analgesics, zinc oxide, vitamin A, vitamin E, or extracts of *Harpagophytum procumens* (Devil's claw) root, *Salix Alba* (White Willow) plant and/or bark, *Tanacetum Parthenium* (Feverfew) herb and/or flower, *Equisetum arvense* (Horsetail), *Spireae ulmaria* (Dropwort), *Betula alba* (Birch), *Urtica dioica* (Stinging Nettle), *Curcumin* extract, *longa* (Tumeric), marine algae, Gotu kola (*Centella asiatica* Linn.), total triterpenic fraction of *Centella asiatica* (TTECA) or a combination thereof.

In addition, the composition described herein may comprise one or more additional non-plant component, for example, but not limited to Lanolin, petroleum jelly (e.g. Vaseline™), Paraffin oil, Zinc oxide, cod liver oil, vegetable oil, paraffinium liquid, and one or more preservative, for example, but not limited to hydroxybenzoates, or scent agents to camouflage the odor of the formulation, for example, but not limited to essential oils of plants/flowers, or any combination thereof.

Without wishing to be limiting in any manner, the composition may be formulated into a suitable topical dosage form, for example, but not limited to an ointment, lotion or cream that may be applied topically to a wound or site of skin injury as such. More preferably, the composition is formulated into ointments for applying to wounds. For example, but not wishing to be limiting in any manner, an ointment comprising 2% oil from the leaves of *Melaleuca alternifolia* (Tea Tree oil); 2.8% gum from the resin of *Boswellia serrata* (*boswellia*); 1% of a 10% gel from the leaves of *Aloe vera* (*Aloe*); 0.4% oil from the flower of *Lavandula officinalis* (Lavender), Lanolin, Zinc oxide, Cod Liver oil, Paraffinum Liquidum, Vaseline™ White, Propyl hydroxybenzoate, Methyl hydroxybenzoate, and water can be prepared using standard procedures known in the art. The composition may also comprise additional components including, but not limited to, alginate, hydrocolloid and or other components.

In a further non-limiting embodiment of the invention, the plant ointment is prepared by warming the lanolin (9 kg), Vaseline™ (9 kg) and paraffin (10 kg) together to +/−55° C. so the mix is a fluid liquid. Ten kg of a 22% concentrate of *Boswellia serrata* gum or resin, Tea Tree oil (*Melaleuca* oil), *Aloe vera* gel, and Lavender oil (*Lavandula officinalis*) is prepared and warmed to 30-35° C. and a clear liquid is obtained. After that, the first liquid is added in a tub (pit) with a mixer, thereafter the second liquid is added (warmed Lurax concentrate). In a preferred embodiment, the mixer is a high power mixer with sufficient power to mix the reagents, although it does not have to turn quickly, similar to a dough-kneader. Once well mixed (e.g. after approximately 10-15 minutes), approximately 7.2 kg of zinc oxide may be added. After 5 minutes of further mixing, the warm ointment can be filled into a container.

In another non-limiting embodiment, there is provided a composition to obtain a wound dressing or wound foam comprising 2% oil from the leaves of *Melaleuca alternifolia* (Tea Tree oil); 2.8% gum from the resin of *Boswellia serrata* (*boswellia*); 1% gel from the leaves of *Aloe vera* (*Aloe*); 0.4% oil from the flower of *Lavandula officinalis* (Lavender), Lanolin, Zinc oxide, Cod Liver oil, Paraffinum Liquidum, Vaseline™ White, Propyl hydroxybenzoate, Methyl hydroxybenzoate, Water and an absorptive agent such as, but not limited to, calcium alginate, chitosan or hydrocolloid (natural, chemically modified, and/or synthetic hydrocolloids).

In a further embodiment, there is provided a composition comprising 2% oil from the leaves of *Melaleuca alternifolia* (Tea Tree oil); 2.8% gum from the resin of *Boswellia serrata* (*boswellia*); 1% gel from the leaves of *Aloe vera* (*Aloe*); 0.4% oil from the flower of *Lavandula officinalis* (Lavender), Lanolin, Zinc oxide, Cod Liver oil, Paraffinum Liquidum, Vaseline™ White, Propyl hydroxybenzoate, Methyl hydroxybenzoate, Water and an absorptive agent such as, but not limited to, calcium alginate, chitosan or hydrocolloid (natural, chemically modified, and/or synthetic hydrocolloids) and this composition is added to, coated or embedded into a fibrous wound dressing, bandage or other type of dressing for applying directly to wounds.

It is intended that the present invention includes additional embodiments of the specific preparations and preparative methods described above. Variations according to the knowledge of one skilled in the art such as by scale, i.e. by scaling-up or scaling-down the described parameters. Further, the specified time and temperature ranges specified above should be considered to be exemplary for the purpose of enabling one to practice the invention, and therefore non-limiting.

The present invention also contemplates a method of treating wounds, sun burns, heat burns, skin injuries, insect bites, surgical incision wounds, traumatic wounds, cracked heals, skin ulcers, diabetic ulcers, pressure ulcers or other skin injury conditions and the like by administering a composition, ointment or dressing composition as described herein to a subject in need thereof. In a preferred embodiment, which is not meant to be limiting in any manner, it is generally preferred that the composition, ointment or dressing composition, as described herein, be applied daily until the wound is closed/healed.

Definitions:

A "dressing" is an adjunct used for application to a wound to promote healing and/or prevent further harm. It is designed to be in direct contact with the wound. The dressing may be a piece of material, such as cloth or gauze, a film, a gel, a foam, chitin, a hydrocolloid, an alginate, a hydrogel, or a polysaccharide paste, granules or beads. Dressings can be impregnated with any desired antiseptic chemicals, an agent designed to speed healing, or other active agent as is known in the art or described herein.

A "bandage" is a piece of material used either to support a medical device such as a dressing, or on its own to provide support to the body. Bandages may take a wide range of forms, from generic cloth strips, to specialized shaped bandages designed for a specific limb or part of the body. In certain embodiments, a "bandage" may also refer to a supporting material and a dressing which is used directly on a wound.

"Chitin" is a polymer comprising units of N-acetyl-D-glucos-2-amine covalently linked with β-1,4 linkages. Medical devices as described herein may comprise chitin in order to take advantage of its properties as a flexible and strong material, as well as its biodegradability. In certain embodiments, chitin may be incorporated into a dressing, or other non-limiting medical device.

A "hydrocolloid" is defined as a colloid system wherein the colloid particles are dispersed in water. A hydrocolloid has colloid particles spread throughout water, and depending on the quantity of water available that can take place in different states, e.g., gel or sol (liquid). Hydrocolloids can be either irreversible (single-state) or reversible. Hydrocolloids can be derived from natural or synthetic sources. Non-limiting examples of natural hydrocolloids include agar-agar, carrageenan, gelatin, and pectin. In hydrocolloid-based medical dressings, the hydrocolloid may interact with tissue fluid to form a nonadhesive gel.

"Alginate" is a salt of alginic acid, typically extracted from marine kelp. Certain alginates, including but not limited to calcium, sodium, and ammonium alginates, can be used in foam, cloth, or gauze for absorbent surgical dressings.

vehicle group at each measurement time point. Differences are considered statistical significance at P<0.05. CGS-21680 ((2-p-carboxyethyl)phenylamino-5'-N-carboxamidoadenosine) was used as a positive comparator.

Test substance C-T-1001 (Ointment A: herbal active ingredients tea tree oil, *boswellia* resin, aloe vera gel and lavender oil) was evaluated for possible wound healing activity. The test substance was applied topically to the wound area once, twice, or three times daily for 10 consecutive days. Percent closure of the wound (%) was determined on days 3, 5, 7, 9 and 11 in order to generate the half closure time (CT50). One-way ANOVA followed by Dunnett's test was used to determine significant difference between the treated groups and vehicle control. It was concluded that topical administration of C-T-1001 at 20 mg/mouse for 10 consecutive days promoted significant increase in wound closure during the observation period from day 7 to day 11, in proportion to frequency of daily treatment; C-T-1001 at 20 mg/mouse 2 and 3 times daily, but not once a day treatment, was associated with a significant decrease in CT50 value in the mouse model of cutaneous injury. The results are summarized in Table 1 and FIG. 1.

TABLE 1

Summary of animal test data

| Treatment | Route | Dose | | The Closure of Wound (%) | | | | | $CT_{50}$ |
| | | | | Day 3 | Day 5 | Day 7 | Day 9 | Day 11 | (Days) |
| --- | --- | --- | --- | --- | --- | --- | --- | --- | --- |
| Vehicle | TOP | 20 μl/mouse × 10 | X | 26.7 | 43.0 | 52.8 | 65.9 | 73.2 | 6.9 |
| (1.5% CMC/PBS pH7.4) | | | SEM | 3.4 | 3.0 | 2.2 | 1.9 | 1.9 | 0.3 |
| C-T-1001 | TOP | 20 mg/mouse qd × 10 | X | 9.5 | 25.6 | 54.2 | 77.4* | 88.3* | 6.8 |
| | | | SEM | 2.8 | 2.2 | 3.2 | 1.2 | 1.0 | 0.1 |
| C-T-1001 | TOP | 20 mg/mouse bid × 10 | X | 13.7 | 37.2 | 63.6* | 84.6* | 91.0* | 6.2* |
| | | | SEM | 2.5 | 3.3 | 1.6 | 1.2 | 0.7 | 0.1 |
| C-T-1001 | TOP | 20 mg/mouse tid × 10 | X | 14.2 | 36.5 | 67.9* | 86.0* | 94.9* | 6.0* |
| | | | SEM | 2.9 | 2.5 | 3.1 | 1.7 | 1.3 | 0.1 |
| CGS-21680 | TOP | 10 μg/mouse × 10 | X | 42.4* | 56.3* | 66.8* | 74.3* | 81.7* | 5.5* |
| | | | SEM | 1.7 | 1.5 | 2.3 | 1.3 | 0.6 | 0.1 |

The closure of the wound (%) and wound half-closure time ($CT_{50}$) were determined. One-way ANOVA followed by Dunnett's test was used for comparison between the treated and vehicle groups.
*P < 0.05, vs. vehicle.

The present invention will be further illustrated in the following examples.

EXAMPLES

Animal model: Groups of 8 ICR male mice weighing 22±2 g were used. Under ether anesthesia, the shoulder and back region of each animal was shaved. A sharp punch (ID 12 mm) was used to remove the skin including panniculus carnosus and adherent tissues. The wound area, traced onto clear plastic sheets on days 3, 5, 7, 9 and 11, were quantitated by use of an Image Analyzer (Life Science Resources VISTA, Version 30). Test compound and vehicle (20 μl, 1.5% carboxymethylcellulose in PBS) were applied topically immediately following injury and in single, two or three applications daily thereafter for a total of 10 consecutive days. The wound half-closure time ($CT_{50}$) was determined and unpaired Student's t test was applied for comparison between treated and Human Clinical Trial:

Summary—In a 30-day clinical trial, the benefits of several formulations of the herbal active ingredients tea tree oil, *boswellia* resin, aloe vera gel and lavender oil, on wound healing were assessed in six uniform wounds created by using a fractional $CO_2$ laser in over 30 healthy human volunteers. The formulations were compared and tested on each of the over 30 volunteers. The formulations were applied to wounds daily, and occluded with a bandage dressing, for a period of 30 days. After one week of treatment, hydrophilic ointment formulations performed significantly better than Polysporin™ and Petrolatum for erythema, epithelialization, and maceration. Throughout the 30-day study (days 14, 21) the hydrophilic ointment formulations performed better for erythema. In addition, the hydrophilic ointment formulations performed better than Petrolatum and Polysporin™ for scarring and hyperpigmentation. The study also demonstrated that a higher degree of occlusion would ameliorate the healing of the wound.

Clinical Trial Details—The 30-day controlled trial was conducted to assess the effects for five topically applied agents on wound healing in six uniform wounds created by using a $CO_2$ laser. At Baseline, one negative control site and five test sites were marked on the ventral forearms (three sites per arm) and the Investigator created five uniform wounds, approximately 100 microns deep and 1 centimeter in diameter, using a fractional $CO_2$ laser set at a regular mode at the five test sites; the negative control site was not exposed to the laser. A total of 31 human volunteers completed the study. Five formulations were evaluated in this study. Ointment A: multi-herbal ointment that was more fluid than thick in consistency. Ointment B: multi-herbal ointment that was thick in consistency. Ointments A and B had the exact same quantities of active ingredients and non-medicinal ingredients and the only difference was the blending method that made the ointment thicker. Ointment A and ointment B contained the herbal active ingredients tea tree oil, *boswellia* resin, aloe vera gel and lavender oil. Cream C: multi-herbal topical formulation that also contained the exact same quantity of active ingredients as ointments A and B but it did not contain the same non-medicinal ingredients. Cream C is a hydrophilic formulation. Formulation D: a commercial preparation of Petrolatum. Formulation E: Polysporin™.

After Baseline evaluations, the human volunteers applied the formulations twice daily to the assigned test (the control site was left untreated) site and subsequently (each time) an adhesive bandage was applied over the wound site.

Evaluations were conducted, blinded by the investigator, at Day 1, Day 4, Day 7, Day 14, Day 21, and Day 30. At baseline and Days 1, 4, 7, 14 and 21, evaluations consisted of: grading for erythema, edema, epithelialization, maceration and scabbing. On Day 30, the wounds were visually graded for Scar Formation (Scar Formation (0=healthy, normal skin and 10=keloid, hypertrophic, or other scar present) and Post-Inflammatory Hyperpigmentation (Post-Inflammatory Hyperpigmentation (0=none and 10=severe).

Overall, after one week of treatment, ointments A and B performed better than formulations D and E for erythema, epithelialization, and maceration. At Days 14 and 21, the ointments A and B continued to perform better for erythema. Formulations D and E performed better than ointments A and B for scabbing and hydration, starting after two weeks of treatment. This was due to the highly occlusive nature of test formulations D and E (Petrolatum and Polysporin™, respectively).

Mean values for clinical grading at each time point (Days 1, 4, 7, 14, 21 and 30) were statistically compared to mean Baseline values using analysis of variance (ANOVA) with pair-wise comparisons (Fisher's LSD) and paired t-tests at the $p \leq 0.05$ significance level. Mean percent change from Baseline and incidence of positive responders were calculated for all attributes.

The results are presented in Table 2 below. It should be noted that the Cream C was discontinued from the study due to poor healing during the first week of treatment. The results provided are only for Ointments A and B and Formulations D and E.

TABLE 2

Mean Values For Clinical Grading

| | Treatment | Baseline (n = 31) | Day 1 (n = 31) | Day 4 (n = 31) | Day 7 (n = 31) | Day 14 (n = 31) | Day 21 (n = 30) |
|---|---|---|---|---|---|---|---|
| Erythema | A | 1.87 | 2.16 | 2.94 ○ | 3.48 ○ | 3.84 ○ | 3.77 ○ |
| | B | 1.97 | 2.48 | 2.74 ○ | 3.26 ○ | 3.84 ○ | 4.07 ○ |
| | D | 2.10 | 2.58 | 3.32 ○ | 4.32 ○ | 5.35 ○ | 5.30 ○ |
| | E | 2.10 | 2.81 ○ | 3.39 ○ | 4.61 ○ | 5.06 ○ | 4.98 ○ |
| Edema | A | 0.00 | 0.23 | 0.23 ○ | 0.19 ○ | 0.16 | 0.12 |
| | B | 0.00 | 0.23 ○ | 0.42 ○ | 0.10 | 0.13 | 0.00 |
| | D | 0.06 | 0.19 | 0.55 ○ | 0.55 ○ | 0.35 ○ | 0.12 |
| | E | 0.00 | 0.29 ○ | 0.39 ○ | 0.39 ○ | 0.16 | 0.03 |
| Epithelialization | A | 0.00 | 0.90 ● | 2.32 ● | 3.48 ● | 5.55 ● | 6.65 ● |
| | B | 0.00 | 0.71 ● | 2.06 ● | 3.58 ● | 5.84 ● | 6.83 ● |
| | D | 0.00 | 0.68 ● | 2.06 ● | 2.68 ● | 5.61 ● | 6.33 ● |
| | E | 0.00 | 0.71 ● | 2.45 ● | 2.81 ● | 5.45 ● | 6.68 ● |
| Maceration | A | 0.00 | 0.52 ○ | 1.45 ○ | 1.13 ○ | 0.19 | 0.07 |
| | B | 0.00 | 0.58 ○ | 1.61 ○ | 0.90 ○ | 0.16 | 0.07 |
| | D | 0.00 | 0.68 ○ | 1.90 ○ | 1.26 ○ | 0.26 ○ | 0.43 |
| | E | 0.00 | 0.45 ○ | 1.39 ○ | 1.65 ○ | 0.35 ○ | 0.30 |
| Scabbing | A | 0.00 | 0.00 | 0.13 | 0.94 ○ | 2.55 ○ | 1.32 ○ |
| | B | 0.00 | 0.00 | 0.19 | 0.84 ○ | 1.97 ○ | 1.02 ○ |
| | D | 0.00 | 0.00 | 0.23 | 1.26 ○ | 1.45 ○ | 0.60 ○ |
| | E | 0.00 | 0.00 | 0.00 | 0.71 ○ | 1.97 ○ | 0.60 ○ |

● Indicates a statistically significant ($p \leq 0.05$) improvement compared to Baseline ○ Indicates a statistically significant ($p \leq 0.05$) worsening compared to Baseline Comparisons, based on the average change from the Baseline, were made among the test sites using analysis of variance (ANOVA) with pair-wise comparisons (Fisher's LSD). The rankings shown in Table 3 below are presented from the least to the greatest level of change, which is presented in parentheses. Statistically significant ($p \leq 0.05$) differences between the test materials appear below, and items marked by the same line are not significantly different from one another.

TABLE 3

Comparisons Among Test Sites Based On The Average Change From The Baseline

| | Product Code | Average Change |
|---|---|---|
| Erythema Day 7 $p < 0.0001$ | B | (1.29) |
| | A | (1.61) |
| | D | (2.23) |
| | E | (2.52) |
| Erythema Day 14 $p < 0.0001$ | B | (1.87) |
| | A | (1.97) |
| | E | (2.97) |
| | D | (3.26) |
| Erythema Day 21 $p < 0.0001$ | A | (1.90) |
| | B | (2.03) |
| | E | (2.88) |
| | D | (3.23) |
| Epithelialization Day 7 $p = 0.0003$ | D | (2.68) |
| | E | (2.81) |
| | A | (3.48) |
| | B | (3.58) |
| Maceration Day 7 $p = 0.0123$ | B | (0.90) |
| | A | (1.13) |
| | D | (1.26) |
| | E | (1.65) |
| Scabbing Day 14 $p = 0.0054$ | D | (1.45) |
| | B | (1.97) |
| | E | (1.97) |
| | A | (2.55) |
| Scabbing Day 21 $p = 0.0237$ | D | (0.60) |
| | E | (0.60) |
| | B | (1.02) |
| | A | (1.32) |

Outcome of Human Study:

Test Ointments A and B performed better than Formulations D and E for erythema on Days 7, 14 and 21

Test Ointments A and B performed better than Formulations D and E for epithelialization on Day 7

Test Ointments A and B performed better than Formulation E for maceration on Day 7

Test Formulation D performed better than A for scabbing on Day 14

Test Formulations D and E performed better than Ointment A for scabbing on Day 21

Overall, after one week of treatment, test Ointments A and B performed better than D and E for erythema, epithelialization, and maceration. With extended treatment, test Ointments A and B continued to perform better for erythema.

Test Formulations D and E performed better than A and B for scabbing, starting after two weeks of treatment. This result is due to the highly occlusive nature of test Formulations D and E (Petrolatum and Polysporin™, respectively) and therefore suggests the application of the herbal formulation using semi and full-occlusive devices such as bandages, dressings, etc, as described herein.

REFERENCES

1. Li J, Chen J, Kirsner R. *Pathophysiology of acute wound healing*. Clinics in Dermatology 2007; 25: 9-18.

2. Montesinos, M. C., Gadangi, P., Longaker, M., Sung, J., Levine, J., Nilsen, D., Reibman, J., Li, M., Jiang, C. K., Hirschom, R., Recht, P. A., Ostad, E., Levin, R. I. and Crostein, B. N. *Wound healing is accelerated by agonists of Adenosine $A_2$ ($G\alpha_s$-linked) receptors*. J. Exp. Med. 186: 1615-1620, 1997.

3. Heggers J P, Pelley R P, Robson M C. *Beneficial effects of Aloe in wound healing*. Phytotherapy Research 1993; 7: S48-52.

4. Heggers J P, Kucukcelebi A, Listengarten D, et al. *Beneficial effects of Aloe on wound healing in an excisional wound model*. J Altern Complem Med 1996; 2:271-8.

5. Lansdown A B, Mirastschijski U, Stubbs N, Scanlon E, Agren M S. *Zinc in wound healing: theoretical, experimental, and clinical aspects*. Wound Repair Regen. 2007 January-February; 15(1):2-16.

6. Denis Okan, Kevin Woo Elizabeth A. Ayello R. Gary Sibbald. *The Role of Moisture Balance in Wound Healing* Adv Skin Wound Care 2007; 20:39-53; quiz 54-5.

7. Terkelsen L H, Eskild-Jensen A, Kjeldsen H, Barker J H, Hjortdal V E. *Topical application of cod liver oil ointment accelerates wound healing: an experimental study in wounds in the ears of hairless mice*. Scand. J Plast. Reconstr. Surg. Hand Surg. 2000; 34:15-20.

What is claimed is:

1. A composition for treating sores, wounds, burns or other traumatized dermal tissues and skin injuries, formulated into a topical ointment, lotion or cream comprising about 2% by weight oil from the leaves of *Melaleuca alternifolia* (Tea Tree oil); about 2.8% by weight gum from the resin of *Boswellia serrata* (boswellia); about 1% by weight to about 10% by weight gel from the leaves of *Aloe vera* (Aloe); and about 0.4% by weight oil from the flower of *Lavandula officinalis* (Lavender).

2. The composition of claim 1, further comprising Lanolin, Zinc oxide, Cod Liver oil, Paraffinum Liquidum, white petroleum jelly, Propyl hydroxybenzoate, Methyl hydroxybenzoate and water.

3. The composition of claim 2, further comprising an alginate, a hydrocolloid, or combinations thereof.

4. The composition according to claim 1, wherein the composition comprises about 50% to 79% by weight boswellic acids.

5. The composition according to claim 1, wherein the Tea Tree oil contains at least 10% by weight terpinene-4-ol.

6. The composition according to claim 1, further comprising one or more component or extract containing growth factors; an antibiotic; an analgesic; zinc oxide; vitamin A; vitamin E; an extract of *Harpagophytum procumens* (Devil's claw) root, *Salix Alba* (White Willow) plant or bark, *Tanacetum Parthenium* (Feverfew) herb or flower, *Equisetum arvense* (Horsetail), *Spireae ulmaria* (Dropwort), *Betula alba* (Birch), *Urtica dioica* (Stinging Nettle), *Curcuma, longa* (Tumeric), marine algae or *Gotu kola* (*Centella asiatica* Linn.); total triterpenic fraction of *Centella asiatica* (TTECA);

or combinations thereof.

7. The composition according to claim 6, wherein the component or extract containing growth factors comprises colostrum, whey, blood, tissue, or combinations thereof.

8. The composition according to claim 1, further comprising a component to absorb wound exudates, slowly release the active agents, or both.

9. The composition according to claim 8, wherein the one or more components to absorb wound exudates, slowly release the active agents or both is selected from the group consisting of alginate, chitosan, hydrocolloid, chitin, polyoligosaccharide, liposome, a slow-releasing polymer or agent, and combinations thereof.

10. The composition of claim 9, wherein the hydrocolloid comprises a natural, chemically modified, or synthetic hydrocolloid, or a combination thereof.

11. The composition of claim 9, wherein the alginate comprises calcium alginate.

12. The composition of claim 1, further comprising one or more non-plant component selected from the group consisting of Lanolin, petroleum jelly, Paraffin oil, Zinc oxide, cod liver oil, vegetable oil, and paraffinium liquid.

13. The composition of claim 1, further comprising a preservative.

14. The composition of claim 13, wherein the preservative is a hydroxybenzoate.

15. The composition of claim 1, further comprising a scent agent to camouflage the odour of the composition.

16. The composition of claim 15, wherein the scent agent comprises an essential oil of a plant, flower, or combination thereof.

17. The composition of claim 1, added to, coated on or embedded into a wound dressing or bandage.

18. The composition of claim 17, wherein the wound dressing is a fibrous wound dressing or a dressing for applying directly to wounds for occlusion or semi-occlusion.

19. The composition of claim 1, formulated within or on the surface of a medical device.

20. The composition of claim 19, wherein the medical device is a dressing, a bandage, or other semi-occlusive or occlusive material used in wound care.

21. A medical device comprising the composition as defined in claim 1, coated thereon or embedded within said medical device.

22. The medical device of claim 21, wherein the composition is contained at least partially within particles or microparticles.

23. The medical device of claim 22, wherein the particles or microparticles are liposomes.

24. The medical device of claim 22, wherein the particles or microparticles comprising the composition are used to deliver or release active ingredients to the wound while maintaining semi-occlusion or complete occlusion.

25. The medical device of claim 21, wherein the medical device is a dressing, a bandage, or other semi-occlusive or occlusive material used in wound care.

26. A method of treating sores, wounds, burns or other traumatized dermal tissues and skin injuries, comprising administering a composition as defined in claim 1 to a subject in need thereof.

27. The method of claim 26, wherein the composition is applied daily until there is at least partial healing or amelioration of the sore, wound, burn or other traumatized dermal tissue or skin injury.

28. The method of claim 26, wherein the method comprises treating acute wounds selected from the group consisting of heat burns, sun burns, traumatic injuries, surgical wounds, punctures, cracked heals, bites, insect bites and infected wounds.

29. The method of claim 26, wherein the method comprises treating chronic wounds selected from the group consisting of venous leg ulcers, pressure sores or ulcers, ischemic ulcers and diabetic ulcers.

30. The method of claim 26, wherein the subject is a mammal.

31. The method of claim 30, wherein the mammal is a human.

* * * * *